(12) United States Patent
Hayakawa (10) Patent No.: US 12,012,325 B2
(45) Date of Patent: Jun. 18, 2024

(54) CONTENT FILLING SYSTEM AND VERIFICATION METHOD OF CONTENT FILLING SYSTEM

(71) Applicant: Dai Nippon Printing Co., Ltd., Tokyo (JP)

(72) Inventor: Atsushi Hayakawa, Tokyo (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 0 days.

(21) Appl. No.: 17/653,150

(22) Filed: Mar. 2, 2022

(65) Prior Publication Data

US 2022/0185645 A1 Jun. 16, 2022

Related U.S. Application Data

(62) Division of application No. 16/497,517, filed as application No. PCT/JP2018/012807 on Mar. 28, 2018, now Pat. No. 11,332,356.

(30) Foreign Application Priority Data

Mar. 28, 2017 (JP) ................. 2017-063516

(51) Int. Cl.
*B67C 7/00* (2006.01)
*A61L 2/18* (2006.01)
(Continued)

(52) U.S. Cl.
CPC ............ *B67C 7/0073* (2013.01); *A61L 2/186* (2013.01); *B29C 49/42* (2013.01); *B65B 55/10* (2013.01); *B67C 2003/227* (2013.01)

(58) Field of Classification Search
CPC ....... A61L 2/186; B67C 7/0073; B29C 49/42; B65B 55/10
See application file for complete search history.

(56) References Cited

U.S. PATENT DOCUMENTS

| 2011/0094616 A1 | 4/2011 | Hayakawa et al. |
| 2011/0133370 A1 | 6/2011 | Engelhard et al. |

(Continued)

FOREIGN PATENT DOCUMENTS

| CN | 102282093 A | 12/2011 |
| CN | 105636758 A | 6/2016 |

(Continued)

OTHER PUBLICATIONS

English translation for WO 2010/090247 (Year: 2010).*

(Continued)

*Primary Examiner* — Sean E Conley
(74) *Attorney, Agent, or Firm* — BURR PATENT LAW, PLLC (57) ABSTRACT

A preform is sterilized by a preform sterilizer. The preform is blow-molded by a blow-molding device to manufacture a container. Next, the container is filled with a culture medium by a filling device without sterilizing the container by a container sterilizer, and the container is plugged by a plugging device. Thereafter, it is verified how much microorganism survive or propagate in the culture medium in the container. A degree of sterilization in the container sterilizer is adjusted on the basis of a verification result.

3 Claims, 4 Drawing Sheets

(51) Int. Cl.
*B29C 49/42* (2006.01)
*B65B 55/10* (2006.01)
*B67C 3/22* (2006.01)

(56) References Cited

U.S. PATENT DOCUMENTS

| | | |
|---|---|---|
| 2014/0311095 A1 | 10/2014 | Hayakawa et al. |
| 2015/0027088 A1 | 1/2015 | Miyahara et al. |
| 2016/0257054 A1 | 9/2016 | Hayakawa et al. |
| 2016/0257055 A1 | 9/2016 | Hayakawa et al. |
| 2017/0348893 A1 | 12/2017 | Ueda et al. |

FOREIGN PATENT DOCUMENTS

| | | |
|---|---|---|
| EP | 2 394 950 A1 | 12/2011 |
| EP | 3 070 010 A1 | 9/2016 |
| JP | H11-035016 A1 | 2/1999 |
| JP | 2009-280222 A1 | 12/2009 |
| JP | 2013-189232 A1 | 9/2013 |
| JP | 2014-080207 A1 | 5/2014 |
| JP | 2015-116816 A1 | 6/2015 |
| JP | 2016-107998 A1 | 6/2016 |
| WO | 2010/016539 A1 | 2/2010 |
| WO | WO 2010/090247 * | 8/2010 |
| WO | 2013/061956 A1 | 5/2013 |

OTHER PUBLICATIONS

Japanese Office Action (Application No. 2017-063516) dated May 29, 2018 (with English translation).
Japanese Office Action (Application No. 2017-063516) dated Dec. 21, 2018 (with English translation).
International Search Report and Written Opinion (Application No. PCT/JP2018/012807) dated Jun. 5, 2018.
English translation of International Preliminary Report on Patentability (Chapter I) (Application No. PCT/JP2018/012807) dated Oct. 10, 2019.
Japanese Office Action (Application No. 2019-051615) dated Mar. 6, 2020 (with English translation).
Extended European Search Report (Application No. 18777727.1) dated Jan. 22, 2021.
Chinese Office Action (Application No. 202111002265.1) dated Aug. 10, 2022 (with English translation).

* cited by examiner

CONTENT FILLING SYSTEM AND VERIFICATION METHOD OF CONTENT FILLING SYSTEM

CROSS REFERENCE TO RELATED APPLICATIONS

This application is a division of U.S. application Ser. No. 16/497,517, filed Sep. 25, 2019, which is the National Stage of International Application No. PCT/JP2018/012807, filed Mar. 28, 2018, which designated the United States, the entireties of which are incorporated herein by reference.

FIELD OF THE INVENTION

The present invention relates to a content filling system and a verification method of the content filling system.

BACKGROUND OF THE INVENTION

Conventionally, there is known an aseptic filling system in which a molding device to manufacture a container (PET bottle) by blow-molding a preform and a filling device to fill the molded container with a content after the container is sterilized are integrated (for example, see Patent Literature 1). Specifically, in the aseptic filling system, the container molded in the molding device is conveyed to the filling device. In the filling device, the container is sprayed with a hydrogen peroxide aqueous solution as a disinfectant. Thereafter, the solution is dried to sterilize the container. Then, the sterilized container is filled with a content.

However, in the aseptic filling system of the related art, first $H_2O_2$ of 30 μL/EA or more and 50 μL/EA or less is attached in the container in order to achieve a high sterilization effect. Next, a large amount of $H_2O_2$ attached in the container is removed by blowing, for example, hot air for 4 seconds. The reason why the time for blowing the hot air is lengthened is because there is a concern about that the container contracts in a case where a large amount of hot air is blown in a short time. Therefore, it is needed that a small amount of hot air is blown to the container over a relatively long time in order to prevent the thermal contraction of the container. Therefore, there is a problem in that the sterilization device of the aseptic filling system becomes large, and the costs of the aseptic filling system such as an initial cost, a running cost, and maintenance are hardly reduced. In addition, to reduce the amount of used $H_2O_2$ for sterilizing the container is preferable from a viewpoint of reduction in running cost and environmental protection.

CITATION LIST

Patent Literature

Patent Literature 1: JP 2009-280222 A

SUMMARY OF THE INVENTION

The present invention has been made in view of the above problem, and an object thereof is to provide a verification method of a content filling system, and the content filling system which can suppress the cost of a content filling system and reduce the amount of used disinfectant.

According to the present invention, there is provided a verification method of a content filling system which includes a preform sterilizer which sterilizes a preform, a blow-molding device which manufactures a container by blow-molding the preform sterilized by the preform sterilizer, a container sterilizer which sterilizes the container manufactured by the blow-molding device, a filling device which fills the container sterilized by the container sterilizer with a content, and a plugging device which plugs the container filled with the content by the filling device. The method includes a step of sterilizing the preform by the preform sterilizer, a step of blow-molding the preform by the blow-molding device to manufacture the container, a step of filling the container with a culture medium by the filling device without sterilizing the container by the container sterilizer, a step of plugging the container by the plugging device, a step of verifying how much microorganism survive or propagate in the culture medium in the container, and a step of adjusting a degree of sterilization in the container sterilizer on the basis of a verification result.

According to the verification method of the content filling system of the present invention, the preform sterilizer sterilizes or sanitizes the preform by chemical spraying, chemical rinsing, steam, sterile water, sterile air, an electronic beam, an X-ray, or an ultraviolet ray.

According to the verification method of the content filling system of the present invention, the container sterilizer sterilizes or sanitizes the container by chemical spraying, chemical rinsing, steam, sterile water, sterile air, an electronic beam, an X-ray, or an ultraviolet ray.

According to the verification method of the content filling system of the present invention, the step of adjusting the degree of sterilization in the container sterilizer includes a step of adjusting a spraying amount of a chemical agent in the container sterilizer.

According to the verification method of the content filling system of the present invention, the step of adjusting the degree of sterilization in the container sterilizer includes a step of setting a sterilization performance of the container sterilizer such that a value $\Sigma R_2$ becomes $(H_0 - \Sigma R_1 + \Sigma I) - FSO$ or more (herein, $H_0$ is an initial microorganism level of the preform, $\Sigma R_1$ is a microorganism reducing level on the preform by the preform sterilizer, $\Sigma I$ is an increase in level of microorganism on the preform or the container between immediately after the preform sterilizer and immediately before the container sterilizer, $\Sigma R_2$ is a microorganism reducing level on the container by the container sterilizer, and FSO is a target value of a microorganism level on the container after the container passes through the container sterilizer).

According to the present invention, there is provided a verification method of a content filling system which includes a container sterilizer which sterilizes a container, a filling device which fills the container sterilized by the container sterilizer with a content, a plugging device which plugs the container filled with the content by the filling device with a cap, a first cap sterilizer which sterilizes the cap, an air rinse device which air-rinses the cap sterilized by the first cap sterilizer, and a second cap sterilizer which sterilizes again the cap air-rinsed by the air rinse device. The method includes a step of sterilizing the container by the container sterilizer, a step of filling the container with a culture medium by the filling device, a step of sterilizing the cap by the first cap sterilizer, a step of air-rinsing the cap by the air rinse device, a step of plugging the container with the cap by the plugging device without sterilizing the cap by the second cap sterilizer, a step of verifying how much microorganism survive or propagate in the culture medium in the container, and a step of adjusting a degree of sterilization in the second cap sterilizer on the basis of a verification result.

According to the present invention, there is provided a content filling system includes a preform sterilizer which sterilizes a preform, a blow-molding device which manufactures a container by blow-molding the preform sterilized by the preform sterilizer, a container sterilizer which sterilizes the container manufactured by the blow-molding device, a filling device which fills the container sterilized by the container sterilizer with a content, and a plugging device which plugs the container filled with the content by the filling device. FSO is −12 or more and −5 or less to satisfy a relation of $H_0 - \Sigma R_1 + \Sigma I - \Sigma R_2 \leq FSO$ (herein, $H_0$ is an initial microorganism level of the preform, $\Sigma R_1$ is a microorganism reducing level on the preform by the preform sterilizer, $\Sigma I$ is the increase in level of microorganism on the preform or the container between immediately after the preform sterilizer and immediately before the container sterilizer, $\Sigma R_2$ is a microorganism reducing level on the container by the container sterilizer, and FSO is a target value of a microorganism level on the container after the container passes through the container sterilizer).

According to the present invention, it is possible to suppress the cost of the content filling system, and reduce the amount of used disinfectant.

DETAILED DESCRIPTION OF THE INVENTION

First Embodiment

Figure 1:
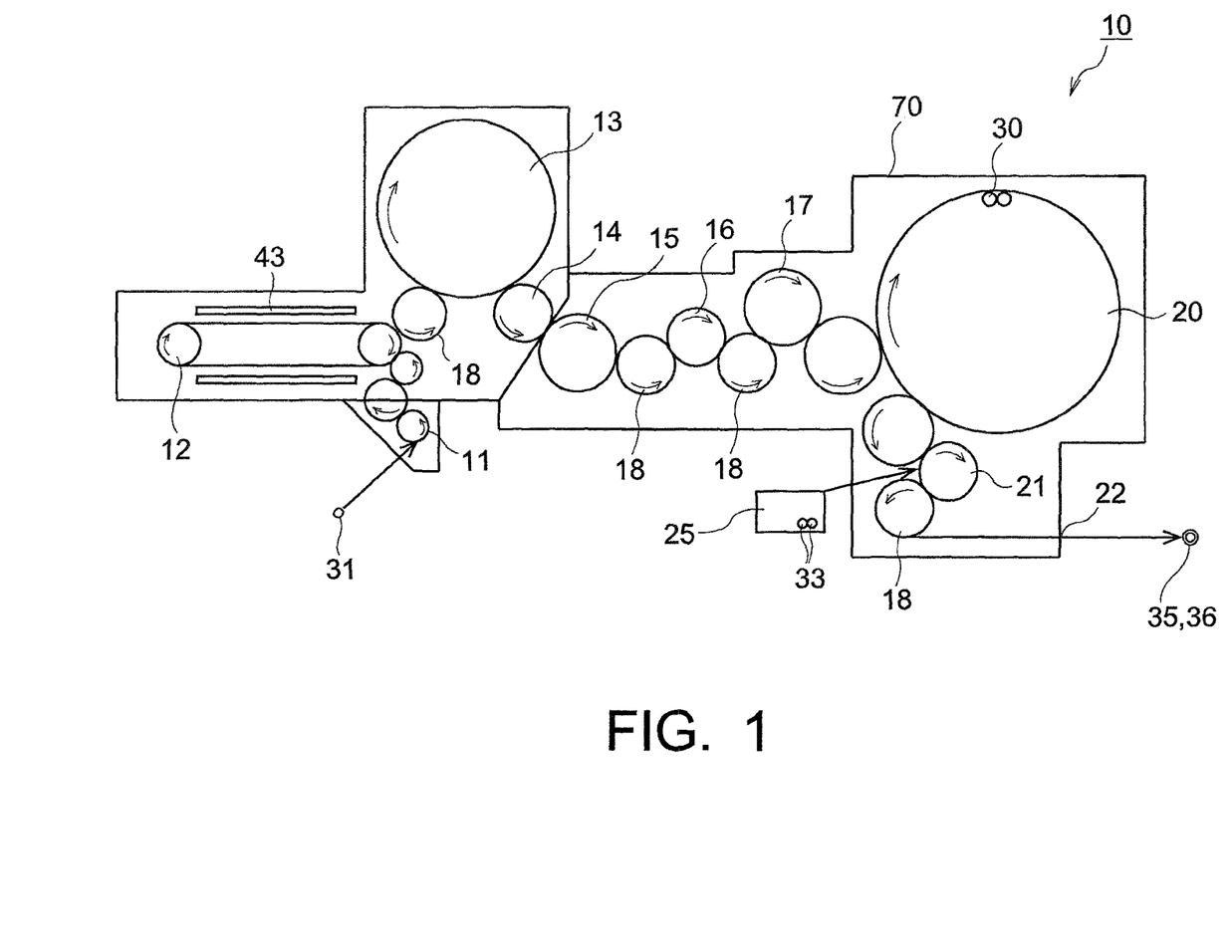
FIG. 1 is a schematic plan view illustrating a content filling system which performs a verification method of the content filling system according to a first embodiment of the present invention.
Figure 2A:
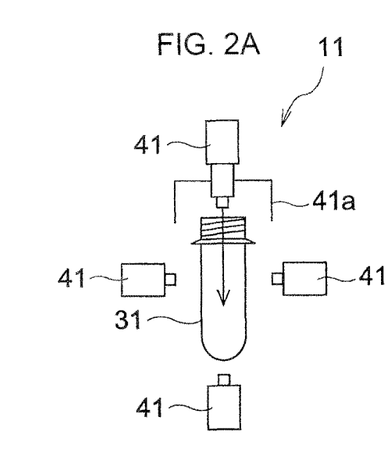
FIGS. 2A-2G are schematic views illustrating a content filling step in the content filling system.
Figure 2B:
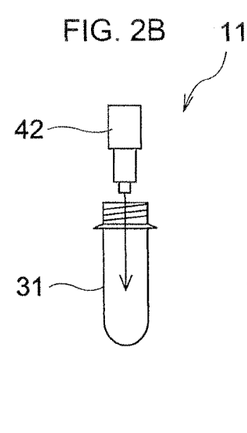
Figure 2C:
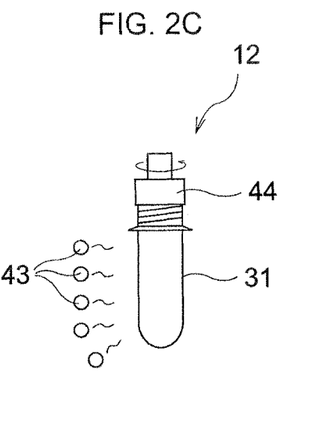
Figure 2D:
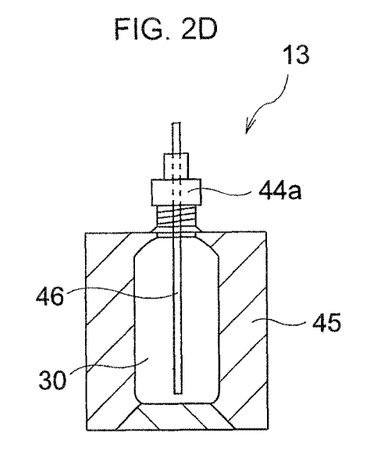
Figure 2E:
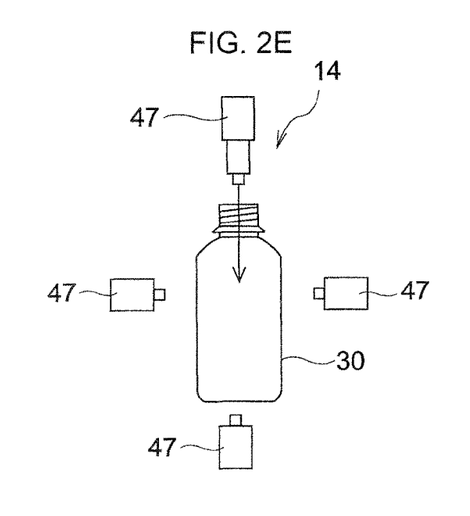
Figure 2F:
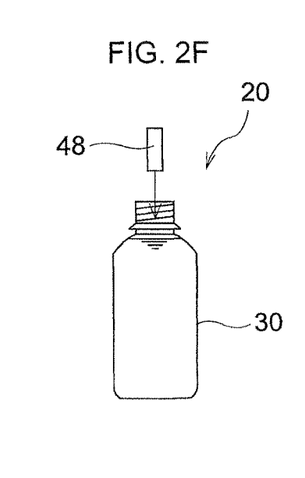

Hereinafter, a first embodiment of the present invention will be described with reference to FIGS. 1 to 3. FIGS. 1 to 3 illustrate the first embodiment of the present invention.
(Content Filling System)

First, a content filling system (sterile filling system, aseptic filling system) according to the present embodiment will be described with reference to FIG. 1.

A content filling system 10 illustrated in FIG. 1 is a system which manufactures a bottle (container) 30 by molding a preform 31 which is manufactured by injecting and molding a synthetic resin material in a biaxial orientation blow, and fills the bottle 30 with a content such as a beverage. Materials of the preform 31 and the bottle 30 are preferably a thermoplastic resin such as polyethylene (PE), polypropylene (PP), polyethylene-terephthalate (PET), or polyethylene naphthalate (PEN).

The content filling system 10 includes a preform sterilizer 11, a preform heating device 12, a blow-molding device 13, a container inspection device 14, a container sterilizer 15, an air rinse device 16, a container rinse device 17, a filling device 20, and a plugging device 21. The preform sterilizer 11, the preform heating device 12, the blow-molding device 13, the container inspection device 14, the container sterilizer 15, the air rinse device 16, the container rinse device 17, the filling device 20, and the plugging device 21 are arranged in this order from the upstream side toward the downstream side. In addition, the plugging device 21 is connected to a cap sterilizer 25 which sterilizes a cap 33 and at the same time conveys the cap 33 to the plugging device 21.

In the preform sterilizer 11, a chemical agent such as a hydrogen peroxide aqueous solution is sprayed from a chemical spraying nozzle 41 (see FIG. 2A) which is disposed in the preform sterilizer 11, and sterilizes the preform 31 (preparation sterilization, a first stage sterilization). Specifically, mist or gas of the hydrogen peroxide aqueous solution is sprayed from the chemical spraying nozzle 41 to the preform 31. With this configuration, a condensation film of hydrogen peroxide in term of 35 mass % is attached and formed in the surface of the preform 31 in a range of 0.0035 $\mu L/cm^2$ or more and 0.35 $\mu L/cm^2$ or less. Since the deposition amount of hydrogen peroxide becomes 0.0035 $\mu L/cm^2$ or more, a sufficient sterilization effect can be achieved. On the other hand, since the deposition amount of hydrogen peroxide becomes 0.35 $\mu L/cm^2$ or less, it is possible to prevent molding defects of whitening, spots, wrinkles, and deformation from the bottle in the case of a blow molding. The condensation film of the deposition amount of hydrogen peroxide in terms of 35 mass % with respect to the preform 31 is more preferably 0.007 $\mu L/cm^2$ or more and 0.2 $\mu L/cm^2$ or less. As illustrated in FIG. 2A, the chemical spraying nozzle 41 may be provided not only for the inner surface of the preform 31 but also for the outer surface of the preform 31. In addition, a guide member 41a may be provided at the end of the chemical spraying nozzle 41 to guide the gas or mist of the chemical agent sprayed to the inner surface of the preform 31 to the screw hole of the outer side of the preform 31 so as to be sterilized.

Further, as a chlorine agent, peracetic acid, nitric acid, chlorine agent, sodium hydroxide, potassium hydroxide, ethyl alcohol, alcohols such as isopropyl alcohol, chlorine dioxide, ozonated water, acidic water, and surface active agent may be used as a single body besides hydrogen peroxide, or two or more types thereof may be used by being combined at an arbitrary ratio.

In the preform sterilizer 11, hot air is also blown from a drying nozzle 42 (see FIG. 2B) to dry the preform 31 after the gas or mist of the hydrogen peroxide aqueous solution is blown. With this configuration, the preform 31 is dried, and hydrogen peroxide is partially removed. The amount of hydrogen peroxide in terms of 35 mass % attached to the preform after drying is suitably in a range of 0.0003 $\mu L/cm^2$ or more and 0.35 $\mu L/cm^2$ or less. The deposition amount of hydrogen peroxide becomes 0.0003 $\mu L/cm^2$ or more, so that a sufficient sterilization effect can be achieved. On the other hand, since the deposition amount of hydrogen peroxide becomes 0.35 $\mu L/cm^2$ or less, it is possible to prevent molding defects such as whitening, spots, wrinkles, and deformation from the bottle in the case of a blow molding. The condensation film of the deposition amount of hydrogen peroxide in terms of 35 mass % with respect to the preform 31 is more preferably 0.0004 $\mu L/cm^2$ or more and 0.2 $\mu L/cm^2$ or less. Further, the drying nozzle 42 may be not necessarily provided.

Further, the preform sterilizer 11 may be configured to sterilize the preform 31 with a chemical rinse. In this case, the preform sterilizer 11 may rinse the inside of the preform 31 using, for example, a chemical agent, and air-rinse the preform 31 to remove the chemical agent. The air-rinsing may be performed using sterile air. The air may be blower-air or compressed air. In addition, after the inside of the preform 31 is rinsed by the chemical agent, the preform 31 may be rinsed with water to remove the chemical agent such as peracetic acid. Alternatively, the preform sterilizer 11 may be configured to rinse the inside of the preform 31 with hot water (sterile water).

As a chemical agent, water containing hydrogen peroxide by 1 wt. % or more and 35 wt. % or less, or peracetic acid by 100 ppm or more and 5000 ppm or less, or preferably by 500 ppm or more and 3000 ppm or less. In addition, as a chemical agent, two or more types of the above chemical agents (hydrogen peroxide, peracetic acid, nitric acid, chlorine agent, sodium hydroxide, potassium hydroxide, ethyl alcohol, alcohols such as isopropyl alcohol, chlorine dioxide, ozonated water, acidic water, surface active agent) may be used by combining at an arbitrary ratio. Further, in a case where a solution (hydrogen peroxide concentration: 0.1 wt. % or more and 35 wt. % or less, or preferably 1 wt. % or more and 25 wt. % or less) obtained by diluting hydrogen peroxide water with alcohols such as ethanol is used as a chemical agent, volatility is increased. Therefore, the rinsing air or the rinsing water to remove the chemical agent may be reduced. In addition, any chemical agent may be used as long as the chemical agent inactivates microorganism, and is not limited to the above examples.

In addition, the preform sterilizer 11 may sterilize the preform 31 with steam such as water vapor. In this case, the preform sterilizer 11 may spray the water vapor to the inside of the preform 31 for example, and air-rinse the preform 31. Further, the air-rinsing may be not omitted.

In addition, the preform sterilizer 11 may be configured to sterilize the preform 31 with an electronic beam, an X-ray, or an ultraviolet ray. In this case, the preform sterilizer 11 may be configured to irradiate the inside of the preform 31 with, for example, the electronic beam (EB) or the X-ray, and to air-rinse the preform 31. Further, the air-rinsing may be not preformed. Alternatively, the preform sterilizer 11 may be configured to irradiate the inside of the preform 31 with the ultraviolet ray to sterilize the preform 31.

With reference to FIG. 1, the preform heating device 12 is configured to heat the preform 31 which is sterilized by the preform sterilizer 11. In the preform heating device 12, a heater 43 is disposed in a tunnel shape along a conveyance path of the preform 31. The preform 31 is heated by the heater 43 while running (see FIG. 2C). The preform 31 is evenly heated at about 90° C. to 130° C. in this heating, and enters a heated state to be suitable to a blow molding.

At the time of heating, the preform 31 is evenly heated in a circumferential direction by the heater 43 such that a spindle (or mandrel; not illustrated) 44 (see FIG. 2C) is inserted to the mouth part, hanged in an erected state (or an inverted attitude), and rotated together with the spindle (or mandrel) 44.

In addition, the surface of the preform 31 is pre-sterilized by the heating step. In other words, the preform 31 is dried while being heated in a state where the condensation film of the chemical agent (for example, hydrogen peroxide) is attached. Therefore, the concentration of the hydrogen peroxide aqueous solution attached to the sterilizing surface is increased, so that a high sterilization effect is achieved, and heat-resistant mold or spore forming microorganism are easily sterilized. In addition, even in a case where the preform 31 is treated with the chemical agent by the preform sterilizer 11, and air-rinsed, a small amount of chemical agent is absorbed in the resin of the preform 31. Therefore, the remaining chemical agent is heated together with microorganism in the heating step, and a high sterilization effect is realized. With this configuration, eumycetes such as general microorganism, spore-forming microorganism, and mold/yeast attached to the surface of the preform 31 are preferably sterilized.

The preform 31 heated by the preform heating device 12 so as to enter a heated state suitably to the blow molding and pre-sterilized is conveyed to the blow-molding device 13. In the blow-molding device 13, the preform 31 is molded in a biaxial orientation blow, and molded to the bottle 30.

In the blow-molding device 13, the preform 31 is inserted into a die 45 (see FIG. 2D) which is a molding die for the blow molding. The die 45 enters a mold-clamping state while continuously running at the same speed as the running speed of the preform 31, and enters a mold-open state after the blow molding is performed on the preform 31 in the die 45.

The preform 31 is almost evenly heated such that the entire temperature is increased to a temperature range in the heating step to be suitable to the molding. After the heating step ends, the preform is conveyed to a blow station of the blow-molding device 13, and mounted in the die 45. In addition, a stretching rod 46 (see FIG. 2D) passes through the upper portion of the die 45 and a blow nozzle 44a in the mouth part of the preform 31 so as to be inserted into the preform 31. During which the die 45 runs, for example, a primary blowing air and a secondary blowing air are sequentially blown into the preform 31 through the blow nozzle 44a, and the preform 31 is expanded up to the bottle 30 of a final molded product in a cavity of the die 45. In this way, if the bottle 30 is molded in the die 45, the die 45 opens while running, and a finished product of the bottle 30 is taken out of the die 45.

With reference to FIG. 1, a plurality of conveying mechanisms (conveying wheels) 18 are disposed in the content filling system 10 to convey the preform 31 and/or the bottle 30. Further, the configurations of the preform heating device 12 and the blow-molding device 13 are not particularly limited, and a generally available device may be used. For example, the blow-molding device 13 is not limited to the rotary mechanism as illustrated in FIG. 1, and may be a linear mechanism.

The container inspection device 14 is positioned on the downstream side of the blow-molding device 13, and inspects the bottle 30 which is manufactured by the blow-molding device 13. The container inspection device 14 inspects deformation or scratches of the bottle 30. As such a container inspection device 14, a bottle inspection device which is conventionally used may be employed.

The container sterilizer 15 sterilizes the interior of the bottle 30 by injecting a disinfectant into the bottle 30 (a main sterilization, a second stage sterilization). With this configuration, the bottle 30 is sterilized by a disinfectant before the content is filled, and microorganism spores, nutritive cells, mold, and yeast are sterilized. As the disinfectant, the chemical agent such as a hydrogen peroxide aqueous solution is used. In the container sterilizer 15, mist or gas of the hydrogen peroxide aqueous solution is generated, and the mist or gas is sprayed on inner and outer surfaces of the bottle 30. Since the inside of the bottle 30 is thus sterilized by the mist or gas of the hydrogen peroxide aqueous solution, the inner and outer surfaces of the bottle 30 is sterilized uniformly.

In the container sterilizer 15, the chemical agent such as the hydrogen peroxide aqueous solution is sprayed from a chemical spraying nozzle 47 (see FIG. 2E) disposed in the inner and outer surfaces of the container sterilizer 15, and the bottle 30 is sterilized. Specifically, the mist or gas of the hydrogen peroxide aqueous solution is blown from the chemical spraying nozzle 47 to the bottle 30.

At this time, the heating by the preform 31 and the heat caused from the die is left in the bottle 30. With this heat, the sterilization effect is increased by the mist and gas of the hydrogen peroxide aqueous solution. As described above, the preparation sterilization is performed on the preform 31, and almost the microorganisms attached to the preform 31 are sterilized through the preparation sterilization. Therefore, with the blowing of the mist or gas of the hydrogen peroxide aqueous solution to the bottle 30, microorganism survived at the stage of the preform 31 and a small amount of microorganism mixed into the blow molding step and the conveying step are sterilized in the main sterilization.

Further, the container sterilizer 15 may be configured to sterilize the bottle 30 with a chemical rinse. In this case, the container sterilizer 15 may rinse the inside of the bottle 30 with the chemical agent such as peracetic acid, and rinse the bottle 30 with water (sterile water) to remove the chemical agent such as peracetic acid. Alternatively, the container sterilizer 15 may be configured to rinse the inside of the bottle 30 with hot water of 60° C. or more and 90° C. or less.

In addition, the container sterilizer 15 may be configured to sterilize the bottle 30 with the electronic beam, the X-ray, or the ultraviolet ray. In this case, the preform sterilizer 11 may be configured to irradiate the inside of the bottle 30 with, for example, the electronic beam (EB) or the X-ray, and to air-rinse the bottle 30. Alternatively, the container sterilizer 15 may be configured to sterilize the preform 31 by rinsing the bottle 30 with the sterile air or the sterile water while irradiating the inside of the preform 31 with the ultraviolet ray.

The air rinse device 16 is configured to perform cleaning by blowing the sterile air of 50° C. or more and 180° C. or less (preferably, 70° C. or more and 140° C. or less) to the bottle 30 sterilized by hydrogen peroxide (disinfectant). With this configuration, the hydrogen peroxide attached to the bottle 30 is removed, and a foreign matter is removed. Further, the air rinse device 16 may be not necessarily provided. In addition, the air-rinsing may be performed in a state where the bottle 30 is erected, but the invention is not limited thereto. The air-rinsing may be performed in a state where the bottle 30 is inversed. With this configuration, the removal of the foreign matter can be performed simultaneously.

The container rinse device 17 sterilizes the bottle 30, sterilized by a hydrogen peroxide aqueous solution as a disinfectant, with hot water. Specifically, for example, hot water having a temperature of 65° C. or more and 80° C. or less is supplied into the bottle 30. Further, the container rinse device 17 may be not necessarily provided.

In addition, when sterilizing the bottle 30, the invention is not limited to one sterilization method. Two types of sterilization methods may be combined.

The filling device 20 fills the previously sterilized content from the mouth of the bottle 30 into the bottle 30. This filling device 20 fills the content in the empty bottle 30 from a filling nozzle 48 (see FIG. 2F). In this case, in the filling device 20, the content is filled to the inside of the bottles 30 while a plurality of the bottles 30 are rotated (revolved). This content may be filled into the bottle 30 at room temperature. The content is previously sterilized by heating or the like, cooled to room temperature of 3° C. or more and 40° C. or less, and then filled into the bottle 30.

The plugging device 21 is configured to plug the bottle 30 by mounting the cap 33 to the mouth part of the bottle 30.

Figure 2G:
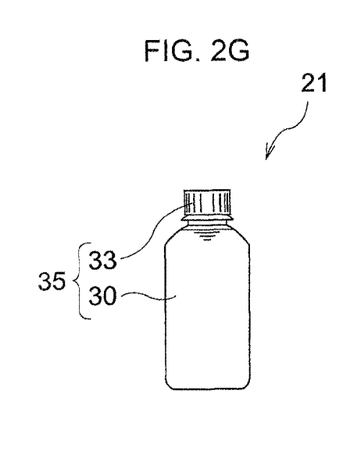
Figure 3:
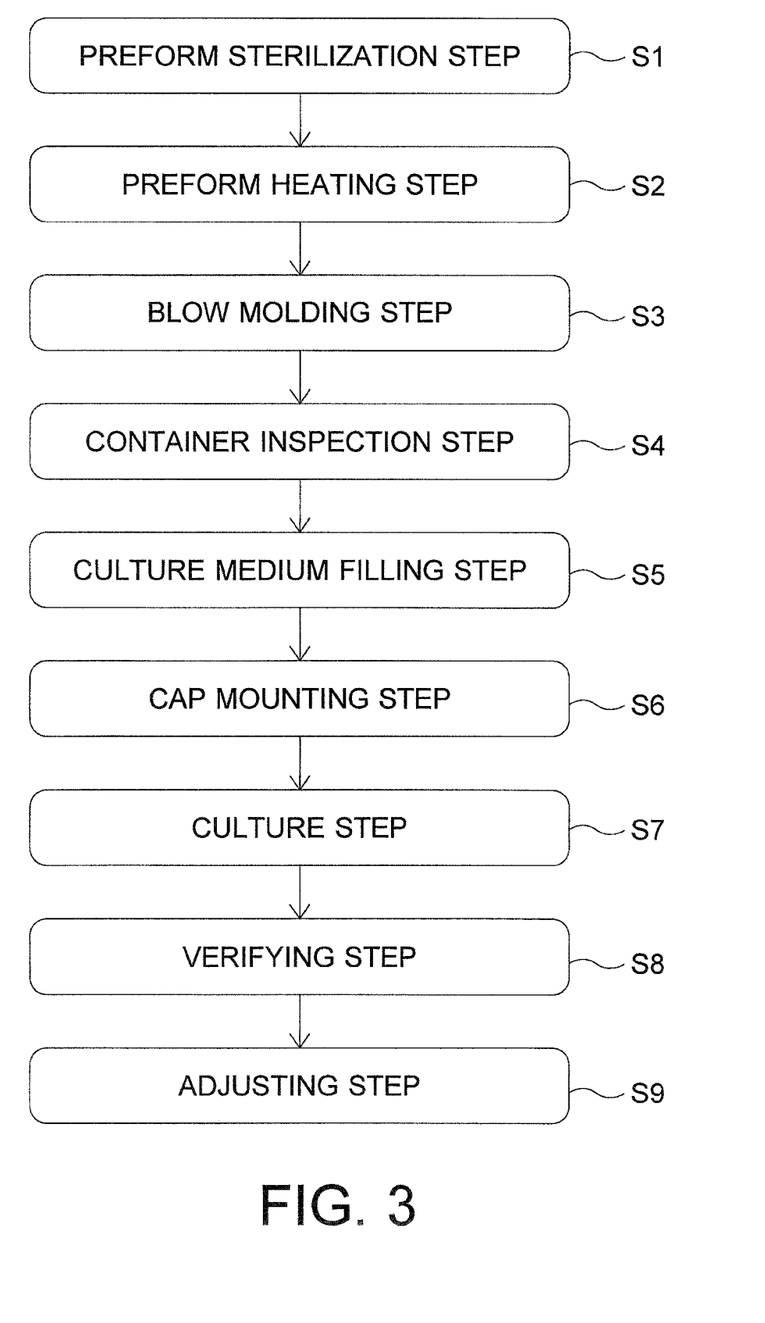
FIG. 3 is a flowchart illustrating the verification method of the content filling system according to the first embodiment of the present invention.

In the plugging device 21, the mouth part of the bottle 30 is plugged by the cap 33, and sealed such that the outer air and microorganisms do not permeate into the bottle 30 (see FIG. 2G). In the plugging device 21, the cap is mounted in the mouth part while a plurality of bottles 30 filled with the content rotates (revolves). Thus, the cap 33 is attached to the mouth of the bottle 30, so that a product bottle 35 is obtained.

A product bottle conveyor 22 is configured to continuously convey the product bottle 35 with the cap 33 mounted by the plugging device 21 toward the outside of the content filling system 10.

In addition, the content filling system 10 includes a sterile chamber 70. The container sterilizer 15, the air rinse device 16, the container rinse device 17, the filling device 20, and the plugging device 21 are stored in the inside of the sterile chamber 70. This content filling system 10 may be, for example, a sterile filling system. In this case, the interior of the sterile chamber 70 is kept in a sterile state.

(Content Filling Method)

Next, a content filling method using the above-described content filling system 10 (FIG. 1) will be described. In the following description, a filling method at a normal time, that is, a content filling method in which a content such as a beverage is actually filled inside the bottle 30 to produce the product bottle 35 will be described.

First, the preform 31 is brought into the preform sterilizer 11. In the preform sterilizer 11, a chemical agent such as a hydrogen peroxide aqueous solution is sprayed from a chemical spraying nozzle 41 (see FIG. 2A) which is disposed in the preform sterilizer 11, and sterilizes the preform 31 (preform sterilization step). Subsequently, in the preform 31, hot air is blown from the drying nozzle 42 (see FIG. 2B) so that the preform 31 is dried, and the sterilization starts while hydrogen peroxide is partially removed.

Next, the preform 31 is sent to the preform heating device 12. In the preform heating device 12, the preform 31 is heated by the heater 43 (see FIG. 2C) while the preform 31 runs (preform heating step). With this configuration, the preform 31 enters a heated state suitable to the blow molding, and the surface thereof is pre-sterilized.

Subsequently, the preform 31 is conveyed to the blow-molding device 13. In the die 45 of the blow-molding device 13 (see FIG. 2D), the preform 31 is biaxially expanded and blow-molded, and is molded to the bottle 30 (bottle molding step).

The bottle 30 manufactured by the blow-molding device 13 is conveyed to the container inspection device 14. Next, the blow-molding device 13 inspects deformation and scratches of the bottle 30 (container inspection step). In a case where there is deformation or scratches in the bottle 30 detected by the container inspection device 14, the bottle 30 discharges the bottle from the container inspection device 14 to the outside of the content filling system 10.

Next, the bottle 30 passed through the container inspection device 14 is sent to the container sterilizer 15. In the container sterilizer 15, the bottle 30 is sterilized using the hydrogen peroxide aqueous solution as a disinfectant (container sterilization step). At this time, the hydrogen peroxide aqueous solution is gas or mist vaporized once at a temperature not less than the boiling point, and is supplied toward the bottle 30. The mist of the hydrogen peroxide aqueous solution is attached to the entire outer surface of the bottle 30, and sterilizes microorganism attached to the bottle 30. The deposition amount of the gas and the mist of hydrogen peroxide supplied into the bottle 30 is preferably a range of 0.01 $\mu L/cm^2$ or more and 0.1 $\mu L/cm^2$ or less in terms of 35 mass %. The deposition amount of hydrogen peroxide becomes 0.01 µL/cm² or more, so that the sterilization effect can be evenly achieved over the entire bottle. On the other hand, if the deposition amount of hydrogen peroxide becomes 0.1 µL/cm² or less, a time taken for the air rinse to remove the remaining hydrogen peroxide becomes not too long, and thus economical. The condensation film of the deposition amount of hydrogen peroxide in terms of 35 mass % with respect to the inner surface of the bottle 30 more preferably falls within 0.03 µL/cm² or more and 0.07 µL/cm² or less.

Subsequently, the bottle 30 is conveyed from the container sterilizer 15 to the air rinse device 16. In the air rinse device 16, the bottle 30 is blown with the sterile air of 50° C. or more and 180° C. or less (preferably, 70° C. or more and 140° C. or less), so that the bottle 30 is cleansed. With this configuration, hydrogen peroxide attached to the bottle 30 is removed, and the foreign matter in the bottle 30 is removed.

Next, the bottle 30 is conveyed from the air rinse device 16 to the container rinse device 17. In the container rinse device 17, the bottle 30 sterilized with hydrogen peroxide (disinfectant) is subjected to sterilization with water or hot water. Specifically, water of a temperature of 10° C. or more and 85° C. or less or hot water is supplied into the bottle 30 at a flow rate of 5 L/min or more and 15 L/min or less.

At this time, it is preferable that the bottle 30 takes an inverted attitude, and the water or hot water is supplied into the bottle 30 through the downwardly opened mouth, and the hot water flows out of the bottle 30 from the mouth. An excess hydrogen peroxide aqueous solution remaining in the bottle 30 and the foreign matter are washed off with the water or the hot water, and discharged from the bottle 30 outward. In some cases, the rinsing may be performed on the outer surface of the bottle 30 with the water or the hot water similarly to the inner surface. Further, such a rinsing step of the container rinse device 17 may be not necessarily provided.

Subsequently, the bottle 30 is conveyed from the container rinse device 17 to the filling device 20. In the filling device 20, the bottle 30 is filled with the content by the filling nozzle 48 (see FIG. 2F) while the bottle 30 rotates (revolves) (filling step). Further, the content is mixed in advance before filled into the bottle 30 by the filling device 20, and a heating sterilization treatment is performed. A heating temperature is about 60° C. or more and 150° C. or less. As a result, microorganisms which may be grown in the product bottle 35 in the content before the filling thereof can be completely sterilized. The content after the heating sterilization treatment is cooled to the room temperature of about 3° C. or more and 40° C. or less. In the filling device 20, the sterilized bottle 30 is filled at the room temperature with the content sterilized and cooled to the room temperature. The temperature of the content during filling is, for example, about 3° C. or more and 40° C. or less.

Subsequently, the bottle 30 filled with the content is conveyed from the filling device 20 to the plugging device 21. Next, in the plugging device 21, the sterilized cap 33 which is sterilized by the cap sterilizer 25 is mounted in the mouth part of the bottle 30, so that the product bottle 35 is obtained (see FIG. 2G) (cap mounting step).

Thereafter, the product bottle 35 is conveyed from the plugging device 21 to the product bottle conveyor 22, and conveyed toward the outside of the content filling system 10.

Further, the steps from the container sterilization step to the cap mounting step are performed in a sterile atmosphere surrounded by the sterile chamber 70, that is, in a sterile environment. After the sterilization treatment, sterile air of positive pressure is supplied into the sterile chamber 70 so that the sterile air is always blown toward the outside of the sterile chamber 70.

In addition, the production (conveying) speed of the bottle 30 in the content filling system 10 is preferably 100 bpm or more and 1500 bpm or less. Here, the conveying speed of the bottle 30 per minute is referred to as bottle per minute (bpm).

(Method for Verifying Content Filling System)

Next, the description will be given about a verification method of the content filling system according to this embodiment to verify a microorganism contamination level of the content filling system 10 (FIG. 1).

The verification method according to this embodiment is configured to check a microorganism contamination level in the content filling system 10, especially, from the preform sterilizer 11 to the container sterilizer 15. This verification method may be performed, for example, at an early stage immediately after the content filling system 10 is completed, that is, before the product bottle 35 starts to be produced when the bottle 30 is filled by actually using the content filling system 10. Alternatively, the verification method may be performed in a case where there is a concern of an influence on the microorganism contamination level such as a case where there occurs a change in a step or a device in the content filling system 10, or in a case where the content filling system 10 has not been used for a while. Alternatively, the verification method may be regularly performed at every filling cycle regardless of the influence of the microorganism contamination level.

In addition, a maintenance work of the content filling system 10 may be performed before the verification method according to this embodiment is performed on an assumption of a case where the microorganism contamination level from the preform sterilizer 11 to the container sterilizer 15 is highest. For example, the die 45, the blow nozzle, and the stretching rod 46 of the blow-molding device 13 may be replaced, or a lamp of the heater 43 of the preform heating device 12 may be replaced. In addition, the works may be performed on an assumption that a maximum number of operators participate in molding and filling.

After the maintenance work is performed, the microorganism contamination level of the content filling system 10 is evaluated, and the verification method according to this embodiment using the bottle 30 filled with a culture medium is performed in order to adjust the degree of sterilization in the container sterilizer 15. Specifically, a number of preforms 31 sterilized by the preform sterilizer 11 is blow-molded by the blow-molding device 13 to manufacture a number of bottles 30. Then, each bottle 30 is filled with a predetermined culture medium instead of the content actually filled therein. Thereafter, it is checked how much the culture medium filled in each bottle 30 is decayed after a predetermined time elapses.

Hereinafter, the verification method of the content filling system 10 according to this embodiment will be described with reference to FIGS. 1 and 3. FIG. 3 is a flowchart illustrating the verification method according to this embodiment.

First, a number of preforms 31 are brought into the preform sterilizer 11 from the outside. Each preform is sterilized in the preform sterilizer 11 (preform sterilization step, step S1 of FIG. 3). The number of preforms 31 used in the verification method of the content filling system 10 is set in advance, and may be 1,000 or more and 300,000 or less for example (preferably, 3,000 or more and 30,000 or less).

Next, each preform 31 is heated by the preform heating device 12 (preform heating step, step S2 of FIG. 3). Then, in the blow-molding device 13, the preform is biaxially expanded and blow-molded so as to form the bottle 30 (blow molding step, step S3 of FIG. 3).

The bottle 30 manufactured by the blow-molding device 13 is inspected in the container inspection device 14 (container inspection step, step S4 of FIG. 3). The bottle 30 passed through the container inspection device 14 is sent to the container sterilizer 15.

Further, each step from the preform sterilization step to the container inspection step is similar to each step from the preform sterilization step to the container inspection step in the normal content filling method described above.

In this case, the container sterilizer 15 is stopped, and the bottle 30 is sent to the filling device 20 without the sterilization of the container sterilizer 15. Further, during that period, the bottle 30 may be blown with the sterile air by the air rinse device 16. Alternatively, the air rinse device 16 is stopped, and the bottle 30 may be sent to the filling device 20 without blowing the sterile air.

In addition, the sterile air may be blown under an air volume condition of the air rinsing in the air rinse device 16 having a foreign matter (microorganism) removing performance as a lower limit (or less than the lower limit) of a production condition.

In addition, in a case where the container rinse device 17 is installed, the bottle 30 is sent to the filling device 20 without the sterilization with water or hot water in the container rinse device 17. Further, during that period, the bottle 30 may be blown with the sterile air by the air rinse device 16. Alternatively, the container rinse device 17 is stopped, and the bottle 30 may be sent to the filling device 20 without blowing water or hot water. In addition, the rinsing may be performed on a flow rate/temperature condition of rinsing with water or hot water in the container rinse device 17 having the foreign matter (microorganism) removing performance as a lower limit (or less than the lower limit) of a production condition.

Next, in the filling device 20, a predetermined amount of culture medium is filled from the mouth part of the bottle 30 into the bottle 30 (culture medium filling step, step S5 in FIG. 3). The culture medium is prepared in advance before filled into the bottle 30 by the filling device 20, and heating sterilization treatment is performed. The pH of the culture medium is adjusted in accordance with the characteristic of the content. For example, the culture medium may be an acid culture medium of 4.0 pH or more and 4.6 pH or less, or may be a neutral culture medium of 6.5 pH or more and 7.5 pH or less.

Such a culture medium is generally formed by dissolving in water 0.2 to 3 wt. % of glucose which is an organic carbon source, monosaccharides such as dextrose, disaccharides, polysaccharides, sodium carbonate, which is an inorganic carbon source, or sodium bicarbonate as a carbon source, 0.5 to 3 wt. % of casein peptone, chicken peptone, cardiac muscle peptone, gelatin peptone, soybean peptone, polypeptone, yeast extract, meat extract, ammonium sulfate, magnesium sulfate, nitrate or the like as a nitrogen source (including coenzyme), and 0.05 to 1 wt. % of sodium chloride, monopotassium phosphate, potassium monohydrogenphosphate, potassium dihydrogenphosphate or the like as a trace mineral or a buffering agent. The pH of the culture medium is adjusted by dissolving hydrochloric acid, tartaric acid, citric acid, sodium hydroxide, potassium hydroxide or the like in the culture medium.

Subsequently, the bottle 30 filled with the culture medium is sent to the plugging device 21. In the plugging device 21, the sterilized cap 33 which is sterilized by the cap sterilizer 25 is mounted in the mouth part of the bottle 30 (cap mounting step, step S6 of FIG. 3). The cap mounting step is executed similarly to the cap mounting step in the ordinary content filling method described above.

In this way, the culture medium is filled into the bottle 30, and the mouth part is tightly plugged with the cap 33, whereby a verification bottle 36 is obtained.

Then, the verification bottle 36 filled with the culture medium is conveyed from the product bottle conveyor 22 to the outside. Thereafter, a plurality of verification bottles 36 are conveyed to a constant temperature storage (not illustrated) maintained at a predetermined temperature of 25° C. or more and 40° C. or less, and left and cultured in the constant temperature storage (culture step, step S7 of FIG. 3). Further, in a case where the product bottle 35 is warmed and sold by a hot bender, it is necessary to check sterility against thermophilic microorganism, and the verification bottle 36 may be cultured at a temperature of 40° C. or more and 65° C. or less.

After a lapse of a predetermined period (for example, three days or more, preferably seven days or more), all the verification bottles 36 are taken out from the constant temperature storage, and how much microorganism survive or propagate in the culture medium in the verification bottle 36 is verified (verifying step, step S8 in FIG. 3). It is assumed that the result obtained in the verifying step corresponds to the microorganism contamination level from the preform sterilizer 11 to the container sterilizer 15. Further, the verifying step is not limited to the verification using the culture medium, and may be performed in replacement of an actual product or an easily decaying product (for example, a milk-containing beverage).

Thereafter, the sterilization degrees in the container sterilizer 15, the air rinse device 16, and the container rinse device 17 are adjusted on the basis of the result in the verifying step (adjusting step, step S9 of FIG. 3). The adjustment of the sterilization degree in the adjusting step may be performed, for example, by appropriately setting the performances of the container sterilizer 15, the air rinse device 16, and the container rinse device 17 (specifically, by adjusting a spraying amount (deposition amount) of the chemical agent in the container sterilizer 15, an air-blow time in the air rinse device 16, an air volume, an air temperature, the temperature of hot water in the container rinse device 17, the volume of hot water, and an amount of used hot water such as a rinsing time). Alternatively, the installation area of the container sterilizer 15, the air rinse device 16, and the container rinse device 17 may be adjusted to shorten the time when the bottle passes through these devices.

For example, the spraying amount of the chemical agent and the amount of used air, water, or hot water may be restricted while keeping sterilization performances required in the container sterilizer 15, the air rinse device 16, and the container rinse device 17 by adjusting the spraying amount of the chemical agent in the container sterilizer 15, the amount of used air in the air rinse device 16, and the amount of used water or hot water in the container rinse device 17. With this configuration, the costs required for sterilization can be reduced, and an environmental load can be alleviated. In addition, since the installation area of the container sterilizer 15, the air rinse device 16, and the container rinse device 17 is saved, the size of the content filling system 10 can be made compact.

Herein, the adjusting step will be described again. In general, there are microorganism already in the preform 31 before brought into the preform sterilizer 11. An initial microorganism level of the preform 31 is set to $H_0$ ($=\log N_0$). In this case, the initial microorganism level $H_0$ of the preform 31 is affected by the sterilization effect (which is reduced by a microorganism reducing level $\Sigma R_1$ ($=\log(N_0/N_{R1})>0$), and becomes an intermediate contamination between immediately after the preform sterilizer 11 and immediately before the container sterilizer 15 (the increase in level of microorganism: $\Sigma I$ ($=\log(N_I)\geq 0$)) of the preform sterilizer 11. Therefore, the microorganism attached to the bottle 30 are increased at a certain ratio. At this time, the microorganism attached to the bottle 30 are reduced again by the sterilization effect (the microorganism reducing level: $\Sigma R_2$ ($=\log(N_f/N_{R2})>0$)) of the container sterilizer 15, the air rinse device 16, and the container rinse device 17. Further, in a step after the filling device 20, it is assumed that the contamination can be ignored because a sterilization filling facility is used. Therefore, if a microorganism level per one bottle after passing through the container sterilizer 15, the air rinse device 16, or the container rinse device 17 falls to equal to or less than a target value (FSO (Food Safety Objective/ISO13409-1996) ($=\log N$)), it can be considered to have no program in the sterility of the content filling system 10. The following expression represents the above description. Further, "$N_0$" represents the initial number of microorganism per one preform, "$N_{R1}$" represents the number of microorganism per one preform after being sterilized by the preform sterilizer 11, "$N_I$" represents the number of microorganism per one bottle after being intermediately contaminated between immediately after the preform sterilizer 11 and immediately before the container sterilizer 15, "$N_{R2}$" represents the number of microorganism per one bottle after being sterilized by the container sterilizer 15, the air rinse device 16, and the container rinse device 17, and "N" represents a target value of the number of microorganism per one bottle after being sterilized by the container sterilizer 15, the air rinse device 16, and the container rinse device 17.

$$H_0 - \Sigma R_1 + \Sigma I - \Sigma R_2 \leq FSO \quad \text{(Expression 1)}$$

In the verification method, since the container sterilizer 15, the air rinse device 16, and the container rinse device 17 are stopped, $\Sigma R_2$ of (Expression 1) becomes 0. Therefore, the result obtained by the verifying step corresponds to the value $H_0 - \Sigma R_1 + \Sigma I$ in (Expression 1). The value is larger than a normal FSO. Therefore, the sterility of the content filling system 10 can be made equal to or less than the target value (FSO) by setting the sterilization performances of the container sterilizer 15, the air rinse device 16, and the container rinse device 17 such that the value $\Sigma R_2$ becomes equal to or more than ($H_0 - \Sigma R_1 + \Sigma I$)−FSO.

According to this embodiment as described above, how much microorganism survive or propagate in the culture medium in the bottle 30 is verified. The sterilization degrees of the container sterilizer 15, the air rinse device 16, and the container rinse device 17 are adjusted on the basis of the verification result. With this configuration, the spraying amount of the chemical agent in the container sterilizer 15, the air-rinsing condition of the air rinse device 16 (temperature, volume, time), or the installation area of the container sterilizer 15, the air rinse device 16, and the container rinse device 17 can be restricted while maintaining the sterilization degree required for the content filling system 10. As a result, a running cost of the content filling system 10 can be reduced, and an environmental load can be alleviated. In addition, the content filling system 10 can be configured compact.

EXAMPLES

Next, specific examples of the present embodiment will be described.

First, the plurality of preforms 31 were sequentially sterilized using the preform sterilizer 11 of the content filling system 10. The each sterilized preform 31 was blow-molded using the blow-molding device 13 to manufacture the bottle 30. Each bottle 30 was sent to the container sterilizer 15, the air rinse device 16, and the container rinse device 17 sequentially, and sent to the filling device 20 without being sterilized by the container sterilizer 15, the air rinse device 16, and the container rinse device 17. Next, the bottle 30 was filled with the culture medium at a room temperature using the filling device 20, plugged with the cap 33, and cultured for one week at 30° C. Further, the number of the cultured bottles 30 was 75,432 in total. After culturing, it was confirmed that there were two bottles 30 of which the culture medium was decayed as a result of inspecting all the bottles 30. Therefore, the number of microorganism per obtained one bottle was estimated at 2/75,432=about $10^{-4}$, and the value $H_0 - \Sigma R_1 + \Sigma I$ was estimated at $\log(10^{-4})=-4$.

On the other hand, the target value (FSO) of the microorganism level in the content filling system 10 is, for example, −7. Therefore, it is considered that a sterilization level of the content filling system 10 can be reached to the target value (FSO=−7) by setting the sterilization performance of the container sterilizer 15 to −4−(−7)=3 LRV (Log Reduction Level), that is, $\Sigma R_2$=3. Thus, the spraying amount of the chemical agent (hydrogen peroxide solution) in the container sterilizer 15 was adjusted to get a spraying amount of 15.2 kg/h in order to set the sterilization performance of the container sterilizer 15 to 3 LRV. It was the spraying amount was reduced by about 40% more than that of the hydrogen peroxide solution used in the conventional container sterilizer 15. Therefore, it was confirmed that the amount of used hydrogen peroxide solution in the container sterilizer 15 can be reduced. In general, a target value of the sterility level in FSO is desirably set within a range of −12 or more and −5 or less, and desirably within a range of −10 or more and −6 or less depending on microorganism to be targeted. If FSO is set higher than −5, safety issues occur. On the other hand, if the sterility rises until FSO becomes a level lower than −12, energy and costs increase which is not economical. In this embodiment, there is also provided the content filling system 10 of which the sterility level ($H_0 - \Sigma R_1 + \Sigma I - \Sigma R_2$) reaches the target value (FSO is −12 or more and −5 or less).

Second Embodiment

Figure 4:
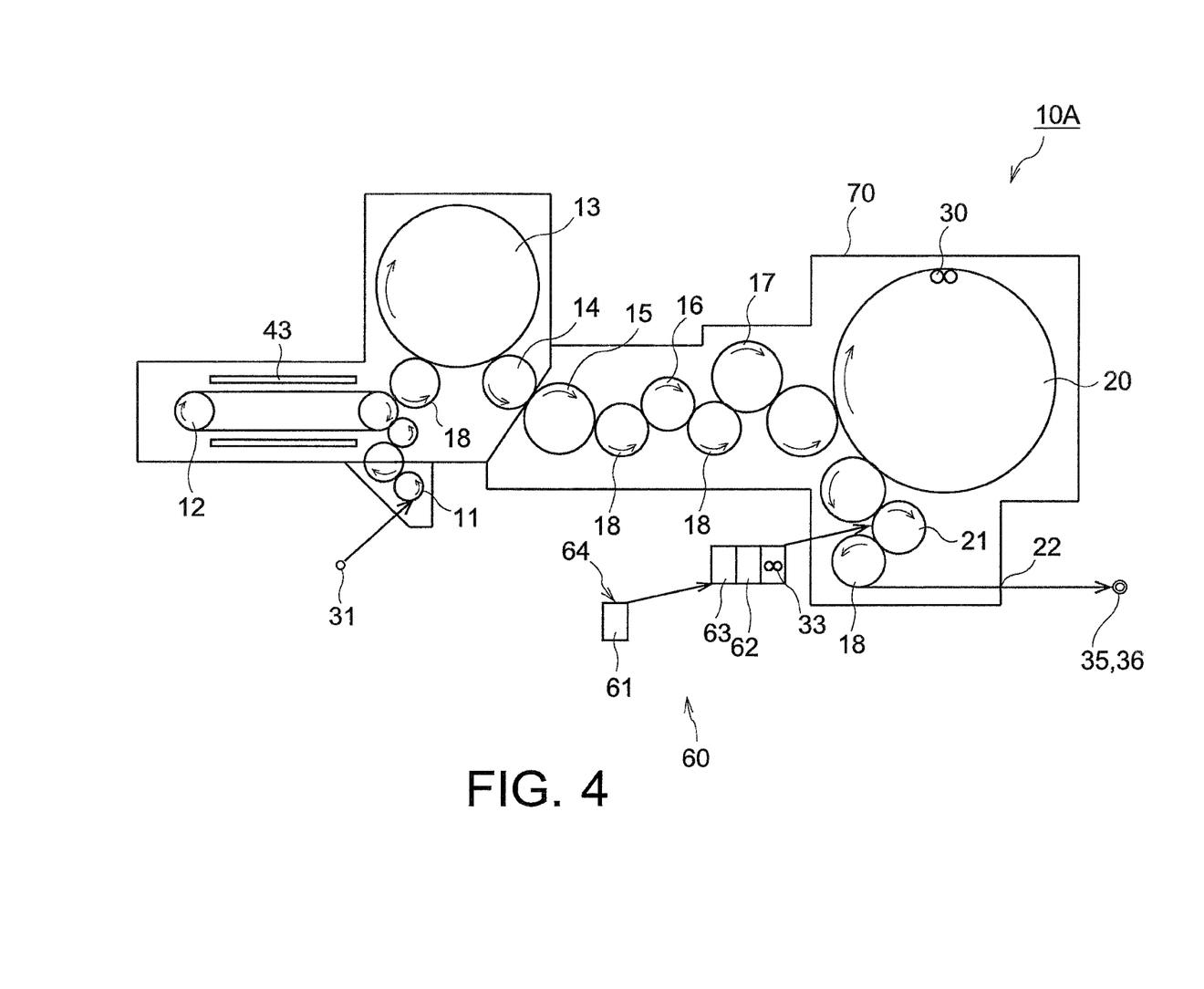
FIG. 4 is a schematic plan view illustrating the content filling system which performs a verification method of a content filling system according to a second embodiment of the present invention.

Next, a second embodiment of the present invention will be described with reference to FIG. 4. FIG. 4 is a diagram illustrating the second embodiment of the present invention. The second embodiment illustrated in FIG. 4 is mainly configured to sterilize the cap 33 in two stages. The same portions in FIG. 4 as those in the first embodiment will be attached with the same symbol, and the detailed description will be omitted.

As illustrated in FIG. 4, a content filling system 10A according to this embodiment includes the preform sterilizer 11, the preform heating device 12, the blow-molding device 13, the container inspection device 14, the container sterilizer 15, the air rinse device 16, the container rinse device 17, the filling device 20, and the plugging device 21. Further, the configurations of the preform sterilizer 11, the preform heating device 12, the blow-molding device 13, the container inspection device 14, the container sterilizer 15, the air rinse device 16, the container rinse device 17, the filling device 20, and the plugging device 21 are almost the same as those illustrated in the first embodiment, and the detailed description will be omitted.

The plugging device 21 is connected to a cap sterilization unit 60 which sterilizes the cap 33 and conveys the sterilized cap 33 to the plugging device 21. The cap sterilization unit 60 includes a first cap sterilizer 61 which sterilizes the cap 33, an air rinse device 62 which air-rinses the sterilized cap 33 by the first cap sterilizer 61, a second cap sterilizer 63 which sterilizes again the cap 33 air-rinsed by the air rinse device 62.

The cap 33 is a well-known cap of which the flat surface is almost a circle shape having an opening on the inner surface side. Further, as the cap 33, high density polyethylene (HDPE), polypropylene (PP), and thermoplastic resin such as biodegradable plastic may be used. In addition, as the cap 33, a composite cap or a sport cap may be used besides a normal bottle cap.

The first cap sterilizer 61 is configured to spray chemical gas or mist such as the hydrogen peroxide aqueous solution to the cap 33 which is conveyed. The deposition amount of hydrogen peroxide required for the first cap sterilizer 61 to sterilize the cap 33 is 0.6 µL/cm$^2$ or more and 4.7 µL/cm$^2$ or less in terms of 35 wt. % (preferably, 1.2 µL/cm$^2$ or more and 2.4 µL/cm$^2$ or less). The first cap sterilizer 61 is installed in a hopper or a sorter 64 which arranges and conveys the randomly inserted caps 33.

The second cap sterilizer 63 is installed on a side near a filling machine, and is configured to spray the chemical gas or mist such as the hydrogen peroxide aqueous solution to the cap 33. The cap 33 is conveyed from the first cap sterilizer 61 up to the second cap sterilizer 63 on a side near the plugging device 21, and is sterilized by the chemical agent such as the hydrogen peroxide aqueous solution.

The air rinse device 62 is installed on a downstream side of the second cap sterilizer 63, and is configured to convey the cap 33 to which the chemical agent is sprayed and to air-rinse the conveyed cap 33. The cap 33 is sequentially conveyed in the air rinse device 62 and, during that, the inner surface and the outer surface of the cap 33 is blown with the sterile hot air. The temperature of the sterile hot air blowing in the air rinse device 62 is, for example, 80° C. or more and 140° C. or less, or preferably 90° C. or more and 120° C. or less. The wind volume of the sterile hot air is, for example, 5 m$^3$/min or more and 20 m$^3$/min or less. In addition, a blow time of the sterile hot air is 0.5 seconds or more and 20 seconds or less, or preferably 1 second or more and 14 seconds or less. When the sterile hot air blows, the temperature of the cap 33 is increased to 40° C. or more, or preferably 50° C. or more. With this configuration, the chemical agent attached to the cap 33 is removed. Further, a minute amount of the component of the chemical agent such as hydrogen peroxide may be contained in the sterile hot air. With this configuration, it is possible to securely remove the chemical agent attached to the cap 33 using the second cap sterilizer 63.

(Cap Sterilization Method)

Next, a cap sterilization method using the cap sterilization unit 60 of the content filling system 10A will be described. Further, the following description will be given about a cap sterilization method at a normal time, that is, a cap sterilization method when the content such as a beverage is filled in the bottle 30 to manufacture the product bottle 35.

First, a number of caps 33 are brought into from the outside of the cap sterilization unit 60. Next, the caps 33 are arranged by the hopper or the sorter 64, and conveyed in the cap sterilization unit 60.

During that period, the cap 33 is sprayed with the chemical agent such as the hydrogen peroxide aqueous solution in the first cap sterilizer 61 installed in the hopper or the sorter 64, and the inner and outer surfaces thereof are sterilized.

Next, the cap 33 is delivered from the first cap sterilizer 61 to the second cap sterilizer 63 on a side near the plugging device 21. Next, in the second cap sterilizer 63, the cap 33 is sprayed with chemical gas as or mist of the chemical agent such as the hydrogen peroxide aqueous solution while being rotatably conveyed, and the inner and outer surfaces thereof are sterilized.

Subsequently, the cap 33 sprayed with the chemical agent is delivered to the air rinse device 62. In the air rinse device 62, the cap 33 is conveyed and, during that, the inner and outer surfaces of the cap 33 with the sterile hot air during conveyed. With this configuration, the chemical agent attached to the cap 33 is air-rinsed.

In this way, in the plugging device 21, the cap 33 sterilized by the cap sterilization unit 60 is mounted in the mouth part of the bottle 30 which is conveyed from the filling device 20. With this configuration, the product bottle 35 which includes the bottle 30 and the cap 33 is obtained.

Thereafter, the product bottle 35 is conveyed from the plugging device 21 to the product bottle conveyor 22, and conveyed toward the outside of the content filling system 10.

(Method for Verifying Content Filling System)

Next, a verification method of the content filling system 10A will be described.

First, a number of caps 33 are sterilized in the first cap sterilizer 61 (first sterilization step of the cap). The number of caps 33 used in the verification method of the content filling system 10A is set in advance. For example, the number of caps may be 1,000 or more and 300,000 or less (preferably, 3,000 or more and 30,000 or less).

Next, the cap 33 is delivered from the first cap sterilizer 61 to the second cap sterilizer 63. In this case, the second cap sterilizer 63 is stopped, and the bottle 30 is sent to the air rinse device 62 without being sterilized by the second cap sterilizer 63.

Subsequently, the cap 33 sprayed with the chemical agent is conveyed in the air rinse device 62 and, during that, the inner and outer surfaces of the cap 33 is blown with the sterile hot air. With this configuration, the chemical agent attached to the cap 33 is air-rinsed. Thereafter, the cap 33 is sent from the air rinse device 62 to the plugging device 21.

On the other hand, similarly to the case of the first embodiment, the preform 31 is sterilized in the preform sterilizer 11, and biaxially expanded and blow-molded in the blow-molding device 13 to be molded to the bottle 30. The bottle 30 is subjected to the sterilization step in the container sterilizer 15.

Subsequently, in the filling device 20, a predetermined amount of culture medium is filled from the mouth part of the bottle 30 into the bottle 30, and the bottle is sent to the plugging device 21. The cap 33 sent from the air rinse device 62 is mounted in the mouth part of the bottle 30 in the plugging device 21. In this way, the culture medium is filled into the bottle 30, and the mouth part is tightly plugged with the cap 33, whereby a verification bottle 36 is obtained.

Then, the verification bottle 36 filled with the culture medium is conveyed from the product bottle conveyor 22 to the outside. Thereafter, a plurality of verification bottles 36 is conveyed to the constant temperature storage which is maintained at a predetermined temperature of 25° C. or more and 40° C. or less, and left and cultured in the constant temperature storage.

After a lapse of a predetermined period (for example, 3 days or more, or preferably 7 days or more), all the verification bottles 36 are taken out of the constant temperature storage, and how much microorganism survive or propagate in the culture medium in the verification bottle 36 is verified. A result obtained by the verification is considered to especially correspond to the microorganism contamination level between the first cap sterilizer 61 and the second cap sterilizer 63.

Thereafter, the degree of sterilization in the second cap sterilizer 63 is adjusted on the basis of the verification result. The adjustment of the degree of sterilization may be, for example, appropriately setting the performance of the second cap sterilizer 63, and specifically adjusting the spraying amount of the chemical agent in the second cap sterilizer 63. Alternatively, an installation area of the second cap sterilizer 63 may be adjusted, and the time taken for the bottle to pass through these devices may be shortened.

In this way, the spraying amount of the chemical agent and the amount of used hot water are restricted while maintaining the sterilization performance required for the second cap sterilizer 63 by appropriately adjusting the spraying amount of the chemical agent in the second cap sterilizer 63. Therefore, the cost required for sterilization can be reduced, and the environmental load can be reduced. In addition, since the installation area of the second cap sterilizer 63 can be reduced, the size of the content filling system 10A can be compact.

In addition, the above embodiments have been described about a system in which the preform sterilizer 11 for the preparation sterilization is installed in the inlet of the blow-molding device 13, and the blow molding and the filling of the content are performed while continuously conveying, but the invention is not limited thereto. The blow-molding device 13 and the filling device 20 are separately disposed, the bottle 30 may be conveyed by an air conveyance or conveyed by a belt conveyor therebetween. In addition, the preform sterilizer 11 for the preparation sterilization is not necessarily provided on a pre-process side of the heater 43, but may be provided in the heater 43, or the conveying wheel 18 located on a post-process side of the heater 43, or in the blow-molding device 13. In addition, the preform sterilizer 11 may be not connected to the blow-molding device 13, and may be provided on a conveyor or a chute of the preform 31. Further, the preform sterilizer 11 may be replaced with an injection molding machine of the preform 31. In this embodiment, the description has been described about the verification method in the two stages of the preparation sterilization of the preform sterilizer 11 and the main sterilization of the container sterilizer 15, but the invention is not limited thereto. The sterilization may be performed through three or more stages.

In addition, the sterilization method of the container is not limited to the methods described in the embodiments. However, any method may be employed as long as microorganism are inactivated, and as long as microorganism are physically sanitized. Further, in the embodiments, a contamination section from the blow-molding device 13 to the container sterilizer 15 may be set as a space where microorganisms are managed using a sterilization filter, and an additional sterilization device may be installed.

The invention claimed is:

1. A content filling system, comprising:
a preform sterilizer which sterilizes a preform;
a blow-molding device which manufactures a container by blow-molding the preform sterilized by the preform sterilizer;
a container sterilizer which sterilizes the container manufactured by the blow-molding device;
a filling device which fills the container sterilized by the container sterilizer with a content;
a plugging device which plugs the container filled with the content by the filling device; and
a cap sterilization unit connected to the plugging device and which sterilizes a cap and conveys a sterilized cap to the plugging device,
wherein the preform sterilizer comprises
a chemical spraying nozzle, which sterilizes the preform by spraying a hydrogen peroxide, and
a drying nozzle which dries the preform after the hydrogen peroxide is sprayed,
wherein an amount of hydrogen peroxide in terms of 35 mass % attached to the preform after drying is in a range of 0.0003 $\mu L/cm^2$ or more and 0.35 $\mu L/cm^2$ or less,
wherein the container sterilizer sterilizes the container by using the hydrogen peroxide as a disinfectant, and
wherein a deposition amount of a gas or a mist of the hydrogen peroxide supplied into the container is a range of 0.01 $\mu L/cm^2$ or more and 0.1 $\mu L/cm^2$ or less in terms of 35 mass %,
wherein the cap sterilization unit sterilizes the cap by using the hydrogen peroxide as a disinfectant, and
wherein a deposition amount of a gas or a mist of the hydrogen peroxide sterilizing the cap in the cap sterilization unit is in a range of 0.6 $\mu L/cm^2$ or less in terms of 35 mass %.

2. The content filling system according to claim 1, wherein the amount of hydrogen peroxide in terms of 35 mass % attached to the preform after drying by using the preform sterilizer, is in a range of 0.0004 $\mu L/cm^2$ or more and 0.2 $\mu L/cm^2$ or less.

3. The content filling system according to claim 1, wherein a guide member is provided at an end of the chemical spraying nozzle, the guide member guiding a gas or mist of the hydrogen peroxide sprayed to an inner surface of the preform, to an outer side of a mouth part of the preform.

* * * * *